United States Patent [19]
de Broqueville

[11] Patent Number: 5,288,934
[45] Date of Patent: Feb. 22, 1994

[54] PROCESS FOR THE CONVERSION OF POLYMERS

[75] Inventor: Axel de Broqueville, Kraainem, Belgium

[73] Assignee: Petrofina, S.A., Brussels, Belgium

[21] Appl. No.: 937,637

[22] Filed: Aug. 27, 1992

[51] Int. Cl.$^5$ .................................. C07C 1/00
[52] U.S. Cl. ............................ 585/241; 585/240; 585/310; 585/324; 585/613; 585/648; 585/653
[58] Field of Search ............ 585/240, 241, 310, 324, 585/613, 648, 653

[56] References Cited

U.S. PATENT DOCUMENTS

| | | | |
|---|---|---|---|
| 3,985,820 | 10/1976 | Albright et al. | 585/648 |
| 4,175,211 | 11/1979 | Chen et al. | 585/241 |
| 4,584,421 | 4/1986 | Saito et al. | 585/648 |
| 4,642,401 | 2/1987 | Coenen et al. | 585/241 |
| 4,851,601 | 7/1989 | Fukuda et al. | 585/241 |
| 5,136,117 | 8/1992 | Paisley et al. | 585/648 |

FOREIGN PATENT DOCUMENTS

| | | |
|---|---|---|
| 0115051 | 8/1984 | European Pat. Off. |
| 0276081 | 7/1988 | European Pat. Off. |
| 0414439 | 2/1991 | European Pat. Off. |
| 207628 | 3/1984 | Fed. Rep. of Germany |
| 2310160 | 12/1976 | France |
| 49-116176 | 11/1974 | Japan |
| 52-084260 | 7/1977 | Japan |

*Primary Examiner*—Patrick P. Garvin
*Assistant Examiner*—E. D. Irzinski
*Attorney, Agent, or Firm*—M. Norwood Cheairs; Jim D. Wheelington

[57] ABSTRACT

Milled polymers are contacted with a liquid which dissolves selectively polystyrene and which separates by specific gravity polyolefins from PET and PVC. Then, at least one of the sorted polymers is converted into lower molecular weight products.

28 Claims, 3 Drawing Sheets

FIG. I

PROCESS FOR THE CONVERSION OF POLYMERS

BACKGROUND OF THE INVENTION

1. FIELD OF THE INVENTION

The present invention relates to the conversion of polymers, particularly the conversion of polymer waste, into industrially useful products. More particularly, it relates to the cracking of polymers mixtures into lower molecular weight products and into light hydrocarbons which can be recycled or used as raw material.

2. DESCRIPTION OF THE PRIOR ART

The polymers are being produced in increasing amounts and most of them are used in the one-use packaging area.

However, the weak tendency of polymers for natural decomposition and the reduction of the number of available rubbish disposal sites lead to search for new directions to treat polymeric material packaging waste.

The incineration is a technique currently used for the treatment of domestic waste. Although it gives good results with polyolefins, due to their complete combustion which gives water and carbon dioxide, this technique is not suitable for other polymers which do not incinerate as well and tend to carbonize and to give off noxious vapors.

The recycling of polymers, as such, only applies for limited applications. Further, it is necessary, after collection, to make a prior sort depending on their nature.

There is thus a need for a polymer conversion process at large scale, particularly a conversion process including cracking mixed polymers waste into lower molecular weight products and into lighter hydrocarbons which can be recycled or used as raw material, for example for supplying oil refineries and petrochemical steam crackers.

The behavior of polymers at high temperature, if need be in the presence of catalysts or appropriate reactants, has been studied for many years and is well known for the person skilled in the art. Depending on the case, it results into depolymerization (for example, for polystyrene pyrolysis or polyethylene terephthalate methanalysis or hydrolysis) or decomposition (for example, during the catalytic treatment of polyethylene).

U.S. Pat. No. 4,151,216 discloses the catalytic cracking of polypropylene at 425°–475° C. on silica-alumina yielding a liquid fuel from 50° C.

U.S. Pat. No. 4,143,086 discloses a fluidized bed catalytic cracking of amorphous polypropylene in the presence of a hydrocarbon feed yielding an effluent containing propylene.

European patent application 414 439 discloses the conversion of high molecular weight polymers into lower molecular weight product by heating the polymer (possibly dissolved) in contact with a zeolitic acid catalyst.

European patent application 276 081 and U.S. Pat. No. 4,584,421 disclose process for the decomposition of polyolefins into two steps; it consists in a thermal cracking followed by a catalytic cracking of the product coming from the first reaction.

However, these processes do not consider the treatment of different polymers mixtures and the resulting problems. It seems, therefore, very important and necessary at this time to have a simple process comprising a minimum amount of steps to treat polymer mixtures. The Applicant has now perfected an integrated process for the conversion of polymers, particularly suitable for the treatment of polymer waste, into industrial useful products.

SUMMARY OF THE INVENTION

According to the present invention, the process for the conversion of polymers comprises at least the steps of:
1) contacting crushed polymers with a liquid which dissolves styrenic polymers but does not dissolve polyolefins, polyethylene terephthalate (PET) and polyvinyl chloride (PVC), and which can separate, according to specific gravity, polyolefins from PET and PVC;
2) separating into :
    a) a fraction comprising dissolved styrenic polymers,
    b) polyolefins, and
    c) a mixture comprising PET and PVC;
3) cracking at least one polymeric material sorted at the preceding step into lower molecular weight products.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Figure 1:
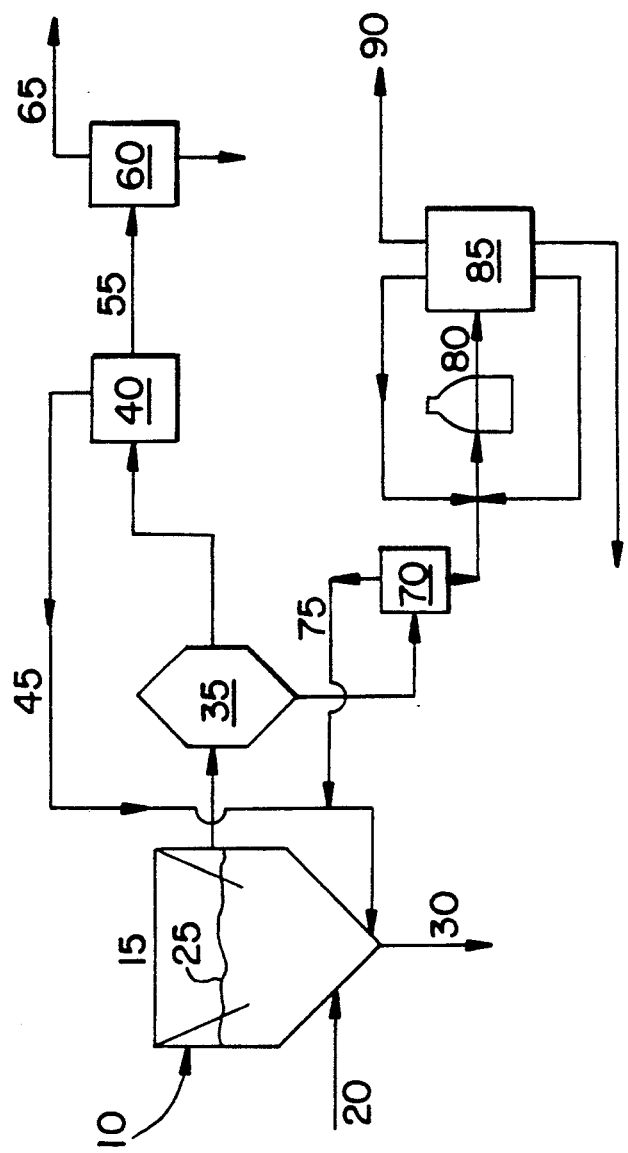
FIG. 1 represents an embodiment of the invention wherein polymers waste coming from crushed packaging is contacted with a mixture of toluene and trichloro-1,1,1 ethane, the insoluble light fraction is separated from the insoluble heavy fraction and the two fractions are treated to recover a hydrocarbon mixture comprising styrene and a hydrocarbon mixture comprising olefins.

The process of the present invention is particularly useful for the treatment of packaging waste. These waste comprise the following polymers :
high and low specific gravity polyethylene (PE);
polypropylene (PP);
polystyrene (PS);
polyvinyl chloride (PVC);
polyethylene terephthalate (PET).

These polymers recovered in the form of films, hollow bodies, dishes or foams are usually not sorted according to their composition.

Before any treatment, it is advisable to crush the polymers into powder or plastic shavings. Although this process does not require any washing when the collection is selective enough, it is advisable to wash, if needed, and to remove the non-polymeric material (paper, metal, etc.).

In the presence of large amounts of insoluble foams in the liquid used for sorting the polymers (mainly, closed cells foams), one can apply a redensification process, such as, for example, the one disclosed in Belgian patent application 897260, which is hereby incorporated by reference.

According one embodiment of the invention, the crushed polymers mixture is put into contact with a liquid able to dissolve, in the existing operating conditions, the styrenic polymers while leaving the polyolefins, PET and PVC in suspension. This liquid has a specific gravity so that polyolefins are separated from PET and PVC according to the specific gravity. The preferred operating conditions range from about room temperature to about the boiling temperature of the liquid, but preferably not much above or below room temperature.

According this embodiment of the present invention, the liquid is a solvent or a mixture of miscible organic solvents having a specific gravity comprised between 0.98 and 1.2, preferably between 1.00 and 1.10. For example, a mixture of trichloro-1,1,1 ethane with toluene, xylene or light cycle oil or dioxane can be used in this invention. Preferably, an equiweighted mixture of trichloro-1,1,1 ethane and toluene which completely dissolves styrenic polymers at room temperature is used. Solvents from the family of ketones can be used in order to reduce the presence of chlorine.

The liquid and crushed polymers flow rates and the contact time are adjusted so that the styrenic polymers are practically totally dissolved in order to obtain a solution as concentrated as possible (usually comprising from 10 to 50% by weight of polymer). The solvent containing the dissolved polystyrene can be recycled until the desired concentration is obtained.

After mixing and decantation, one recovers:
- an insoluble light fraction, comprising polyolefins on the surface layer
- an insoluble heavy fraction, comprising PET and PVC on the bottom, and
- a solution of styrenic polymers.

According to another embodiment of the invention, the crushed polymers are introduced into a container filled with water which contains one or several additives in view to slightly modify its specific gravity to easily separate the polymers into two fractions while not dissolving them:
- the light fraction comprising the styrenic polymers and the polyolefins, and
- the heavy fraction comprising PET, PVC and the heavy polymers.

Since the styrenic polymers have a specific gravity of about 1.03, it is important to adjust the specific gravity of the water to avoid settling of the polymers. For this purpose, the detergents which are already present in the polymer waste may be used and the desired specific gravity may be realized by a further addition of the existing detergent.

Salt water may also be used, the concentration of salt being 4 to 5 g per liter, but it is preferable to use detergents since they reduce sticking of PVC on the polyolefins and, therefore, can be submitted to the usual treatments generally applied to plastic materials.

In a continuous process, the accumulation of detergents in the container should be avoided to reduce unwanted modification of the specific gravity of the water. For this purpose, water in counter current flow may be introduced in the outlet pipe of heavy polymers in order to better control the specific gravity of the liquid in the container.

After mixing and decantation one recovers:
- an insoluble light fraction, comprising polyolefins and styrenic polymers on the surface layer
- an insoluble heavy fraction, comprising PET and PVC on the bottom.

According to a third embodiment of the invention, one uses a mixture of two non-mixable liquids, at a temperature ranging from about 20° C. to about 100° C., and preferably between about 30° C. and about 80° C. For example, the following mixture can be used in the invention:
(1) water
(2) a hydrocarbon solvent The hydrocarbon solvent is selected to have, at the selected temperature, a specific gravity lower than 0.9 and, preferably, between 0.75 and 0.9, while having excellent solvent properties regarding polystyrene but n solvent properties regarding the other polymers, particularly the polyolefins. The specific gravity of the selected solvent should stay, at the operating temperature, lower than 0.9 after dissolution of the styrenic polymers. Examples of suitable solvents are gasoil, naphtha, kerosene, heavy or light cycle oil, heavy gasolines from catalytic cracking and catalytic reforming, aromatic solvents (like toluene, xylene, ethylbenzene) and mixtures thereof. It is preferable to use solvents containing a high proportion of aromatic hydrocarbons. Toluene which is blended with other hydrocarbon boiling in the same boiling range (in order to lower the specific gravity) may be recovered easily by distillation and, therefore, may be preferred, even if it is slightly water soluble.

The crushed polymers are introduced into the container by means of lock filled with water (preferably at the same temperature as the mixture of the two liquids) before being contacted with a solvent lighter than water and non-water mixable. By this way the polymers are separated into two fractions while not dissolving them:
- the light fraction comprising the polyolefins together with the styrenic polymers, and
- the heavy fraction comprising PET, PVC and the heavy polymers.

All these polymers pass thereafter into the container which contains the two non-mixable liquids, wherein only the light fraction, due to its specific gravity, comes into contact with the hydrocarbon solvent which will dissolve the styrenic polymers.

The flow rates of crushed polymers and hydrocarbon solvents as well as the contact time are adjusted in view to obtain, at the selected temperature, a substantial dissolution of the styrenic polymers to achieve a solution containing from 10 to 50% by weight of polymers. The solvent which contains the dissolved polystyrene may be recycled up to obtain the desired concentration.

The amount of water in the container where the contact occurs is not critical. Generally, this amount is equal to that of hydrocarbon solvent. In case of continuous process, the flow rate should be sufficient to compensate the losses and to maintain a constant level at the separation surface. The amount of surface-active agents present in water is adjusted to favor the quick precipitation of the heavy fraction which is water insoluble and to avoid sticking of the PVC on the polyolefins. Accumulation of too high an amount of detergent should be avoided when using the hereabove described procedures.

After the usual operations of mixing, decantation, etc., the light fraction which is insoluble in the solvent (comprising insoluble closed cells foams) is recovered at the surface, while the heavy fraction insoluble in the solvent (comprising PET, PVC and other paper waste) is recovered in the bottom of the water part. On the other side, a fraction comprising the hydrocarbon solvent (with the polymers comprising polystyrene dissolved therein at the selected temperature) and the insoluble polymers (comprising polyolefins) present at the interface water/solvent is recovered.

This fraction is then submitted to a mechanical separation (filtration, centrifugation, decantation or sieving in accordance with particle size of the insoluble polymers) of the insoluble fraction comprising polyolefins from the styrenic polymers solution. The decantation through a counter-current flow of pure solvent is preferred because it allows perfect cleaning of the polyolefins which are in general the most important fractions to recover.

Whatever the embodiment selected for the different steps of contact and separation, one transforms at least a polymer material, separated as described above, into products having lower molecular weights.

According to one embodiment, the styrenic polymers solution is heated to remove traces of water and the major part of the solvent, which is recycled, before sending the polymers (presently melted after their dissolution in the solvent) into a thermal cracking reactor, unless they are converted into pellets for mechanical recycling. The main product of this reaction is styrene, in a mixture comprising normally liquid hydrocarbons. Styrene may be recovered, purified and recycled, while the other hydrocarbons may be recycled in oil refineries or in petrochemical steamcrackers.

According to another embodiment, the insoluble polymers recovered during the mechanical separation, comprising polyolefins alone or styrenic polymers and polyolefins, are heated to eliminate water and solvent which are recycled to the blender. The polymers are then melted and heated to the cracking temperature. The cracking is performed in a catalytic cracking reactor.

According to a preferred embodiment, after the elimination of the solvent, the melted polymer is blended with at least one heavy fraction recycled from the catalytic cracking reactor, said fraction having preferably a boiling point higher than the melting temperature of the polymer, in order to reduce the viscosity of the melt polymer before heating it at the cracking temperature.

The catalysts used, the reaction conditions and the products obtained are well known and described for instance in EP-A-414439, which is hereby incorporated by reference, and there is no need to put a detailed description of them in the present document. These products, mainly normally liquid hydrocarbons, may be recovered, purified and partially recycled as explained hereabove to reduce the viscosity of the melt polymer, or they may be used as raw material in oil refineries or into the petrochemical steamcrackers.

PET which is recovered in the insoluble heavy fraction may be submitted to a treatment of selective decomposition leaving other polymers like PVC, which is the main component of that fraction. This latter polymer may be thermally cracked in the presence of chlorine-fixing agents (like CaO, caustic soda, etc.).

Figure 2:
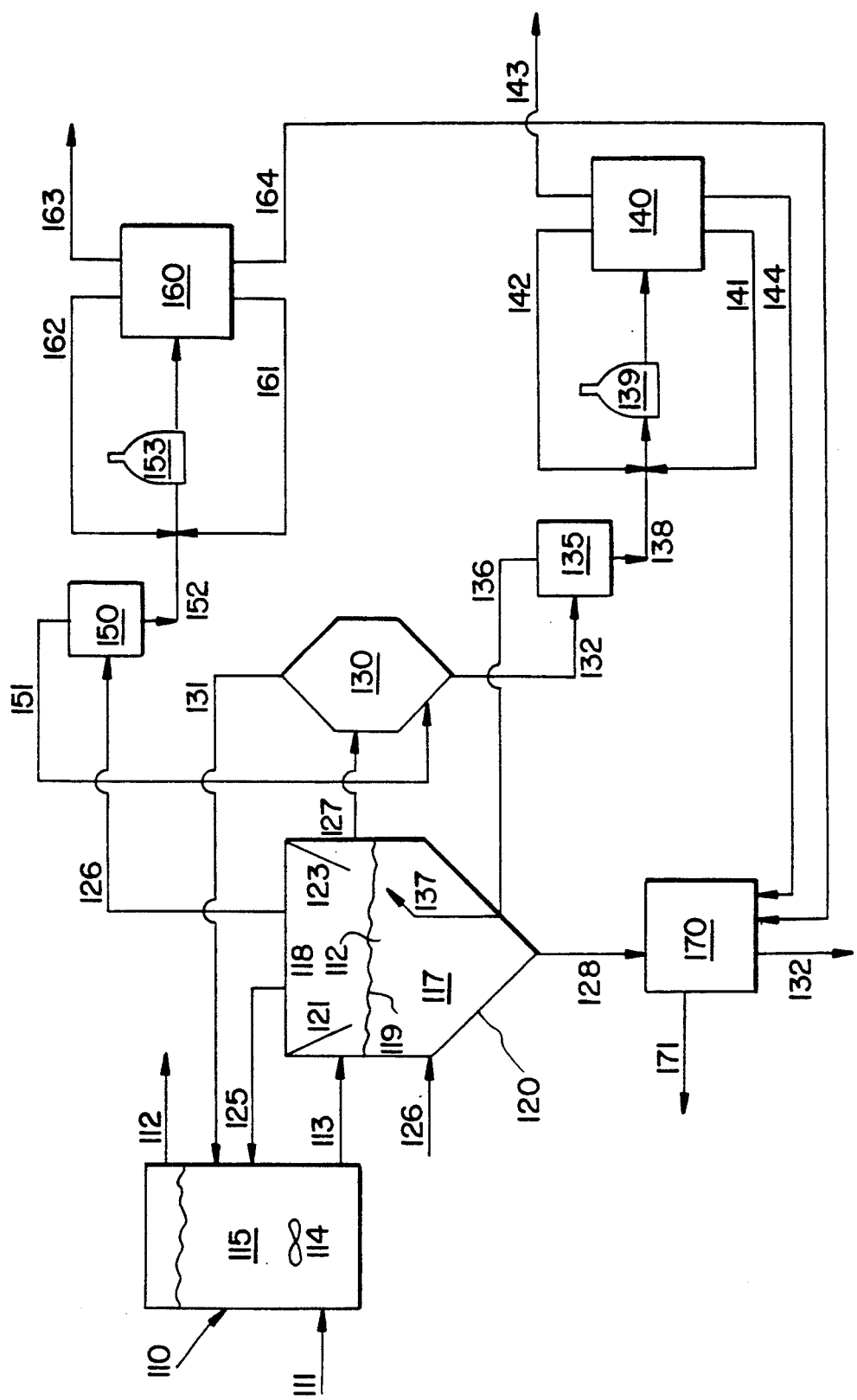
FIG. 2 represents another embodiment of the invention wherein the mixture of crushed polymer waste is contacted with a non-water-soluble polystyrene solvent and streams for polystyrenes, polyolefins and heavy polymers (PVC, PET, etc.) are separated .
Figure 3:
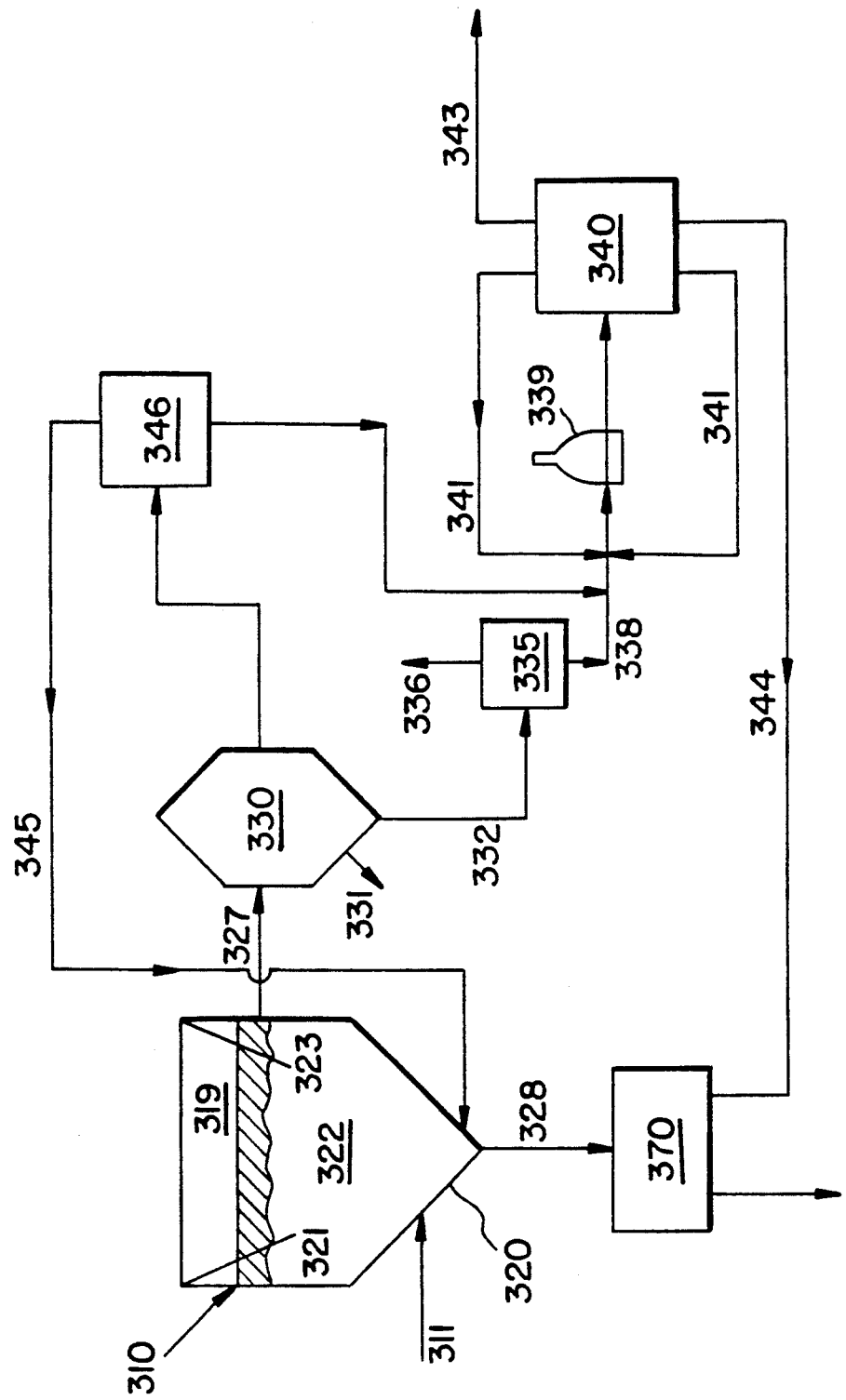
FIG. 3 represents another embodiment of the invention wherein the mixture of crushed polymer waste is contacted with water and a polystyrene solvent, and the polyolefins, the polystyrenes and the heavy polymers (PVC, PET, . . . ) are separated and treated.

The present invention will be described by referring to drawings wherein FIGS. 1, 2 and 3 represent particular embodiments among the numerous possible embodiments.

Referring to FIG. 1, it is shown that polymers waste coming from crushed packaging is sent through the feeding system 10 into a blender 15 where it is put into contact with a mixture of toluene and trichloro-1,1,1 ethane introduced through pipe 20. After mixing and decantation, the insoluble light fraction is recovered on the surface layer 25 while the insoluble heavy fraction is withdrawn through pipe 30.

The fraction comprising the solvent mixture and the polymers dissolved therein is recovered in 35, heated in 40 to eliminate the solvent mixture (recycled through pipe 45) to give a mixture of melt polymer comprising polystyrene, sent through pipe 55 to a thermal cracking reactor 60, wherein a hydrocarbon mixture comprising styrene is recovered in 65.

The insoluble light fraction, comprising polyolefins, is recovered in 25, treated in a dryer 70, (wherein the solvent is withdrawn and recycled via pipe 75), and then melted and sent via pipe 80 into a catalytic cracking reactor 85 from where a hydrocarbon mixture comprising olefins is recovered in 90.

Referring to FIG. 2, the mixture of crushed polymer waste is sent through the feeding system 110 into a dissolving tank 115 where it is put into contact with a solvent of polystyrene which is water-non-soluble and having a specific gravity lower than 0.9, said solvent being introduced through the feeding system 111. After mixing with stirrer 114, the insoluble light fraction is recovered at the surface 112 for suitable treatment (densification or recycling). The solvent containing dissolved styrene polymers and the other polymers in suspension is introduced via pipe 113 into separator 120, optionally provided with baffles 121, 122, 123 to guide the various flows. Said separation is filled half with water 117 fed via pipe 116. In case separator is provided with baffles, it is important that they reach the interface between the two liquids in order to optimize turbulence within the liquids and to improve separation of the polymers.

The solvent 118 may be partially recycled in dissolver tank 115, via pipe 125 to increase the concentration in styrenic polymers dissolved, said solvent is partially withdrawn by pipe 126 and heated in device 150 to separate solvent by pipe 151 from the melt polystyrene which is brought in pipe 152 to be heated more in the oven 153. A purge 164 allows to withdraw the un- reactor 160 wherein a hydrocarbon mixture comprising styrene is recovered through pipe 163.

Some fractions of these hydrocarbons may be recycled through pipe 162 and mixed with melt polymers, in pipe 152 to reduce their viscosity and to increase their speediness through the heating device 153. The non-cracked polymers may be recycled through pipe 161 to the over 5. A purge 164 allows to withdraw the uncrackable residues for further treatment, in reactor 170.

The polyolefins are in suspension along the interface 119 between solvent 118 and water 117. They flow through pipe 127 by gravity to a separation device, for instance a filter or a centrifugation device or as represented on FIG. 2, by a decantation device 130 where solvent is recycled through pipe 131 to dissolver 115. The polyolefins are rinsed by a counter-current of pure solvent brought via pipe 151 in order to limit the impurities flowing with the polyolefins and to minimize the amounts of dissolved polystyrene flowing also with the polyolefins. They are further brought through pipe 132 to a heating device 135 where the pure solvent and water are recovered through pipe 136 and reintroduced into the decanter 120 by means of injection 137 or any other suitable means. Alternatively, water may be separated from solvent and then reintroduced into decanter 120 through pipe 116 and the pure solvent may be reinjected in the bottom of the decanter as additional rinsing means.

The melt polyolefins are brought via pipe 138 to a heating system 139 and then to a catalytic cracking reactor 140 where a hydrocarbon mixture is recovered via pipe 143. Certain fractions of these hydrocarbons may be recycled through pipe 142 and then mixed with melt polyolefins in order to reduce their viscosity and to increase their speediness in the heating system 139. The non-cracked polyolefins can be recycled through pipe 141 to a heating means 139. Then a purge 144 allow to withdraw the non-cracked residues for further treatment in reactor 170. The heavy polymers (PVC, PET, etc) and the other impurities are recovered at the bottom of the decanter via pipe 128 for further treatment.

With respect to heavy polymers such as PVC, PET, etc., various alternatives may be envisioned. A first thermal cracking of PVC at relatively low temperature, e.g. around 300° C., in the presence or absence of material absorbing chlorine such as CaO, followed by a catalytic cracking of PET (hydrolysis or methanolysis). Finally, the non-crackable residues and the various purges will be recovered via pipe 172 to be disposed off optionally after incineration, while the different useful fractions will be recovered via pipe 171.

The material transfer devices noted as 112, 127, 128 and 132 may advantageously comprise a helicoidal screw with variable and/or inclinated pitch allowing concentration of the solid fraction to reduce the flow of liquid.

Referring now to FIG. 3, the mixture of crushed polymer waste is sent through the feeding system 310 into a mixer 320 where it is put into contact with :
  (i) water containing an amount of detergent such that the specific gravity is approximately about 1.04, and
  (ii) a light solvent of the styrenic polymers having a specific gravity lower than 0.9 and which is water insoluble. Water and solvent are introduced via the feeding system 311. The mixer 320 is provided with a stirrer and optionally with baffles 321, 322 and 323.

The olefinic polymers are in suspension at the interface 319 water/solvent. They are flowed via pipe 327 generally by means of gravity to a separation device, such as a filter or a centrifugation device, or as represented on FIG. 3 by a decanter 330 where water is removed via pipe 331. The polyolefins are then sent via pipe 332 to a heating means 335 where water is withdrawn via pipe 336. Alternatively, water may be reintroduced into decanter 320 via pipe 311.

Regarding the styrenic polymers dissolved, the hereabove process may be applied; however, according to another embodiment, the fraction comprising solvent and styrenic polymers dissolved therein is recovered at the outlet of the decanter 330 and send to the heating system 346 for eliminating the solvent (which is recycled via pipe 345) and to give a mixture of melt polymer comprising styrenic polymers sent into pipe 338 to be brought with the polyolefins to the catalytic cracking reactor.

According to this last embodiment, melt polyolefins and melt styrenic polymers are brought through pipe 338 to a heating system 339 and then to the catalytic cracking reactor 340 where a mixture of hydrocarbons is withdrawn via pipe 343. Certain fractions of these hydrocarbons may be recycled via pipe 342 and mixed with the melt polyolefins and melt styrenic polymers in order to reduce their viscosity and to increase their speediness in the heating system 339. The non-cracked polyolefins and styrene polymers may be recycled through pipe 341 to the heating system 339. Finally, a purge 344 allows to eliminate uncrackable residues for further treatment in reactor 370. The heavy polymers (PVC, PET, etc.) and the other impurities are recovered at the bottom of the decanter via pipe 328 for further treatment.

With respect to the heavy polymers, the same process as that described by referring to FIG. 2 may be applied.

It is understood that various modifications may be brought to the embodiments of the process of the invention without being outside of its scope. For instance, the process of the invention may be operated continuously or in batch or semi continuously (e.g. when dissolution is discontinuous and the remaining is continuous). The dissolution operations as well as the separation and decantation of the treated polymers may be performed in one container equipped with suitable means or in one container but according to a step by step process.

An advantage of the process of the invention is the use of a solvent which allows not only to separate the plastics into three groups but also to avoid the use of water to clear the polyolefins which represent the majority of the plastic waste and which have to be relatively pure for the optimal use of catalysts and for the production of good quality hydrocarbons. This invention makes expensive installations for water treatment unnecessary. Indeed, the amount of water used in the process is very small (it is equal to the water flow through pipe 128 and which is not recovered in 170). Further, the presence of a solvent in sufficient amount allows the polymers to be melted by using heat exchangers rather than the mechanical energy of extruders.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

We have taken a 2 kg mixture of worn, soiled and crushed packaging waste, comprising by weight :
  low specific gravity polyethylene 30%
  high specific gravity polyethylene 20%
  polypropylene 20%
  polystyrene 14%
  PVC 8%
  PET 8%
and under the form of (% by weight) :
  bottles, hollow bodies 38%
  dishes 21%
  film 30%
  foam 11%

The waste have been suspended at 30° C. during one hour in a mixture of 50 parts by weight of toluene and 50 parts by weight of trichloro-1,1,1 ethane.

After decantation, three fractions were recovered and dried at 90° C.

The composition was (by weight):
light fraction 68% (polyolefin shavings)
heavy fraction 19% (PVC, PET, non soluble fines and metallic particles shavings)
dissolved fraction 13% (PS)

700 g of these shavings were mixed in a extruder with 100 g of zeolite Y (25% by weight of zeolite Y with a specific surface of 166 m²/g on 75% silica-alumina support. After pelletization, 8 g of the mixture were heated to 450° C. 1.5 g of a gaseous fraction (at 80° C.) and 5.5 g of a liquid fraction (at 80° C.) were recovered.

The analysis of the liquid fraction (at 80° C.) gives the following results:

| distillation: | up to 100° C. | 0.0% by weight |
|---|---|---|
| | 100 to 221° C. | 10.94% by weight |
| | 221 to 350° C. | 67.78% by weight |
| | residue at 350° C. | 21.48% by weight |

The analysis of the gaseous fraction (at 80° C.) gives the following results:

| composition (% by weight): | methane | 0.1 |
|---|---|---|
| | ethylene | 0.2 |
| | ethane | 0.3 |
| | propylene | 4.3 |
| | propane | 0.5 |
| | butene | 13.3 |
| | butanes | 2.1 |
| | pentenes | 23.8 |
| | pentanes | 3.3 |
| | hexenes | 27.7 |
| | hexanes | 6.4 |
| | hydrocarbons C7 and + | 18.0 |

Further the solution of styrenic polymers was recovered and evaporated. 200 g of these polymers were subjected to a thermal cracking at 450° C. 151 g of a liquid fraction and 30 g of a gaseous fraction were recovered.

The analysis of the liquid fraction gives the following results:

| styrene | 52.7% by weight |
|---|---|
| ethylbenzene | 6.7% by weight |
| toluene | 6.0% by weight |
| benzene | 0.1% by weight |
| different lights | 8.9% by weight |
| different heavies | 25.6% by weight |

EXAMPLE 2

We have taken a 2 kg mixture of worn, soiled and crushed packaging waste, comprising by weight:

| high specific gravity polyethylene | 50% |
|---|---|
| polypropylene | 20% |
| polystyrene and SBS | 15% |
| PVC | 10% |
| PET | 5% |
| and under the form of (% by weight): | |
| bottles, hollow bodies | 68% |
| dishes | 24% |
| foam | 8% |

The waste was introduced in water at 80° C. comprising 1% by weight of a surface active agent, and agitated during 20 minutes.

Toluene at 80° C. was slowly added in the container in an amount by weight identical to the water, while avoiding any direct contact with PVC present in the bottom of the container.

Then the toluene containing phase was stirred during 40 minutes while maintaining the temperature at 80° C.

After decantation, four fractions were recovered and dried at 110° C.

The composition was (by weight):

| light fraction above toluene | 0.5% |
|---|---|
| water/toluene interface | 68% (polyolefins shavings) |
| heavy fraction | 19% (PVC, PET, non soluble fines and metallic particle shavings) |
| dissolved fraction | 13% (PS) |

700 g of these shavings were mixed in an extruder with 100 g of zeolite Y (25% by weight of zeolite Y with a specific surface of 166 m²/g on 75% silica-alumina support). After pelletization, 7 g of the mixture were heated to 450° C. 2.5 g of a gaseous fraction (at 80° C.) and 3.5 g of a liquid fraction (at 80° C.) were recovered.

The analysis of the liquid fraction (at 80° C.) gives the following results:

| distillation: | up to 100° C. | 12.38 by weight |
|---|---|---|
| | 100 to 221° C. | 48.65% by weight |
| | 221 to 350° C. | 30.65% by weight |
| | residue at 350° C. | 8.33% by weight |

The analysis of the gaseous fraction (at 80° C.) gives the following results:

| composition (% by weight): | methane | 0.4 |
|---|---|---|
| | ethylene | 0.43 |
| | ethane | 0.7 |
| | propylene | .02 |
| | propane | 1.3 |
| | butenes | 19.64 |
| | butanes | 3.6 |
| | pentenes | 22.24 |
| | pentanes | 3.9 |
| | hexene | 15.48 |
| | hexanes | 1.7 |
| | hydrocarbons C7 and + | 24.54 |

Further the styrenic polymers solution was treated the same way as in example 1 and similar results were obtained after thermal cracking at 450° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter of patent of the United States of America is:

1. A process for the conversion of polymers into recyclable material comprising:
   (1) contacting crushed polymers with a liquid which dissolves styrenic polymers, which does not dissolve polyolefins, polyethylene terephthalate (PET) and polyvinyl chloride (PVC) and which can separate by specific gravity polyolefins from PET and PVC;

(2) separating into:
   (a) one fraction comprising a polymeric material comprising the dissolved styrenic polymers
   (b) one fraction comprising a polymeric material comprising the polyolefins, and
   (c) one fraction comprising a polymeric material comprising a mixture comprising PET and PVC;

(3) cracking at least one polymeric material separated at the preceding step into lower molecular weight products.

2. A process according to claim 1 in which the liquid is a mixture comprising a solvent for the styrenic polymers and water having a specific gravity of about 1.03.

3. A process according to claim 2 in which the mixture additionally comprises additives, said additives being detergents or salts.

4. A process according to claim 1 in which the liquid is a solvent or a mixture of miscible organic solvents having a specific gravity between 1.0 and 1.2.

5. A process according to claim 4, in which the liquid is a mixture of trichloro-1,1,1 ethane and toluene.

6. A process according to claim 1, in which the liquid is a mixture of two liquids comprising at least one hydrocarbon solvent having a specific gravity between 0.75 and 0.9.

7. A process according to claim 6, in which the hydrocarbon solvent comprises toluene, xylene or ethylbenzene and mixture thereof.

8. A process according to claim 1, in which the fraction comprising a polymeric material comprising the dissolved styrenic polymers is cracked by thermal cracking.

9. A process according to claim 2, in which the fraction comprising a polymeric material comprising the dissolved styrenic polymers is cracked by thermal cracking.

10. A process according to claim 3, in which the fraction comprising a polymeric material comprising the dissolved styrenic polymers are cracked by thermal cracking.

11. A process according to claim 4, in which the fraction comprising a polymeric material comprising the dissolved styrenic polymers are cracked by thermal cracking.

12. A process according to claim 5, in which the fraction comprising a polymeric material comprising the dissolved styrenic polymers are cracked by thermal cracking.

13. A process according to claim 6, in which the fraction comprising a polymeric material comprising the dissolved styrenic polymers are cracked by thermal cracking.

14. A process according to claim 7, in which the fraction comprising a polymeric material comprising the dissolved styrenic polymers are cracked by thermal cracking.

15. A process according to claim 11, in which the fraction comprising the polymeric material comprising the polyolefins is cracked by catalytic cracking.

16. A process according to claim 2, in which the fraction comprising the polymeric material comprising the polyolefins is cracked by catalytic cracking.

17. A process according to claim 3, in which the fraction comprising the polymeric material comprising the polyolefins is cracked by catalytic cracking.

18. A process according to claim 4, in which the fraction comprising the polymeric material comprising the polyolefins is cracked by catalytic cracking.

19. A process according to claim 5, in which the fraction comprising the polymeric material comprising the polyolefins is cracked by catalytic cracking.

20. A process according to claim 6, in which the fraction comprising the polymeric material comprising the polyolefins is cracked by catalytic cracking.

21. A process according to claim 7, in which the fraction comprising the polymeric material comprising the polyolefins is cracked by catalytic cracking.

22. A process according to claim 1, in which the fraction comprising the polymeric material comprising the dissolved styrenic polymers and the fraction comprising the polymeric material comprising the polyolefins are cracked by catalytic cracking.

23. A process according to claim 2, in which the fraction comprising the polymeric material comprising the dissolved styrenic polymers and the fraction comprising the polymeric material comprising the polyolefins are cracked by catalytic cracking.

24. A process according to claim 3, in which the fraction comprising the polymeric material comprising the dissolved styrenic polymers and the fraction comprising the polymeric material comprising the polyolefins are cracked by catalytic cracking.

25. A process according to claim 8, in which the polymer fraction subjected to the cracking is melted and conveyed to a cracking reactor from which at least one heavy fraction of the cracked products is recycled to the cracking reactor.

26. A process according to claim 9, in which the polymer fraction subjected to the cracking is melted and conveyed to a cracking reactor from which at least one heavy fraction of the cracked products is recycled to the cracking reactor.

27. A process according to claim 10, in which the polymer fraction subjected to the cracking is melted and conveyed to a cracking reactor from which at least one heavy fraction of the cracked products is recycled to the cracking reactor.

28. A process according to claim 4 in which the liquid is a solvent or a mixture of miscible organic solvents having a specific gravity between 1.05 and 1.10.

* * * * *